United States Patent
Wang

(10) Patent No.: US 10,317,355 B2
(45) Date of Patent: Jun. 11, 2019

(54) ENVIRONMENTAL SENSOR AND METHOD FOR MEASURING AND PREDICTING ENVIRONMENTAL PARAMETERS

(71) Applicant: Goertek.Inc, Shandong (CN)

(72) Inventor: Kun Wang, Shandong (CN)

(73) Assignee: Goertek Inc., Shandong (CN)

( * ) Notice: Subject to any disclaimer, the term of this patent is extended or adjusted under 35 U.S.C. 154(b) by 80 days.

(21) Appl. No.: 15/538,226

(22) PCT Filed: Jul. 23, 2015

(86) PCT No.: PCT/CN2015/084946
§ 371 (c)(1),
(2) Date: Jun. 21, 2017

(87) PCT Pub. No.: WO2016/101610
PCT Pub. Date: Jun. 30, 2016

(65) Prior Publication Data
US 2017/0343499 A1   Nov. 30, 2017

(30) Foreign Application Priority Data
Dec. 25, 2014   (CN) .......................... 2014 1 0822359

(51) Int. Cl.
*G01N 27/12* (2006.01)
*G01N 35/00* (2006.01)
(Continued)

(52) U.S. Cl.
CPC ........... *G01N 27/121* (2013.01); *G01N 35/00* (2013.01); *G05B 13/026* (2013.01); *G05B 19/042* (2013.01); *G05D 23/1917* (2013.01)

(58) Field of Classification Search
CPC ..... G01N 27/121; G01N 35/00; G05B 13/026
See application file for complete search history.

(56) References Cited

U.S. PATENT DOCUMENTS 6,204,623 B1   3/2001   Levy et al.

FOREIGN PATENT DOCUMENTS

| CN | 102042850 A | 5/2011 |
| CN | 103171501 A | 6/2013 |

(Continued)

OTHER PUBLICATIONS

International Searching Authority, International Search Report (ISR) and Written Opinion for International Application No. PCT/CN2015/084946, dated Sep. 25, 2015, 11 pages, State Intellectual Property Office of the P.R.C., China.

*Primary Examiner* — Ryan D Walsh
(74) *Attorney, Agent, or Firm* — Alston & Bird LLP

(57) ABSTRACT

An environmental sensor and an environmental parameter measurement and prediction method, the environmental sensor comprising: a sensing element configured to sense an instant sensing characteristic value, so as to apply sending; an integrated circuit used for continuously obtaining the instant sensing characteristic value and an instant clock signal and obtaining via calculation an instant environmental parameter, so as to apply storing and outputting. A physical and chemical properties function corresponding to the sensing element is provided for the integrated circuit. Under a prediction model, the integrated circuit utilizes the physical and chemical properties function to conduct prediction calculation to obtain an actual environmental parameter, so as to apply storing and sending according to a current instant environmental parameter and an instant clock signal and at least one set of pre-stored instant environmental parameter and instant clock signal.

6 Claims, 3 Drawing Sheets

(51) Int. Cl.
      *G05B 13/02*          (2006.01)
      *G05D 23/19*          (2006.01)
      *G05B 19/042*        (2006.01)

(56) References Cited

FOREIGN PATENT DOCUMENTS

| | | | |
|---|---|---|---|
| CN | 103207633 A | 7/2013 | |
| CN | 104460469 A | 3/2015 | |
| WO | WO-2011162590 A1 * | 12/2011 | ........... G05B 13/026 |

* cited by examiner

ENVIRONMENTAL SENSOR AND METHOD FOR MEASURING AND PREDICTING ENVIRONMENTAL PARAMETERS

CROSS REFERENCE TO RELATED APPLICATIONS

This application is a national stage application, filed under 35 U.S.C. § 371, of International Application No. PCT/CN2015/084946, filed Jul. 23, 2015, which claims priority to Chinese Application No. 201410822359.7, filed Dec. 25, 2014, the contents of both of which as are hereby incorporated by reference in their entirety.

BACKGROUND

The present invention belongs to the technical field of micro electromechanical systems (MEMS), and relates to sensors, in particular to a fast response and calculation method for the sensors.

Sensors are devices used for measuring condition parameters of an external environment. With development of semiconductor technology, various MEMS sensors are also developed. The MEMS sensors have the advantages of small size, light weight, low energy consumption, digital output, and the like, and are convenient for electronic and digital integration. Thus, they are widely applied in numerous fields such as consumer electronics, industrial and agricultural production, environment monitoring, medical treatment, smart homes, automobiles, warehouses, historical relic preservation.

A humidity sensor is a typical MEMS sensor. It reacts to humidity or relative humidity in the environment, which is reflected through an electronic system. But most humidity sensors represented by the MEMS humidity sensors have the problem of low response speed, which is caused by a change speed of variational properties of a humidity-sensitive material. Taking the most common capacitance-type and resistance-type MEMS humidity sensors on the market as an example, most of their response time is more than 6 seconds.

In another aspect, the response time of the humidity sensor is usually in a restriction relationship with precision. A humidity-sensitive material of a high-precision humidity sensor generally has physical and/or chemical property changes to a larger extent. Generally speaking, in order to sufficiently realize the change of a sufficient magnitude, longer time is required. And this limits an application range of the humidity sensor and in turn further limits the application of the humidity-sensitive material with a higher precision.

Therefore, the response speed of the humidity sensors severely restricts its application in environments where humidity change is dramatic and fast measurement is required. As a result, phenomena such as time waste and reduced measurement precision are caused. For intelligent wearing and consumer electronic products, the user experience is greatly reduced. If the environment humidity is changed quickly, it is impossible to realize functions of determining the highest humidity and the like.

The sensors responding to other environmental parameters, such as various gas sensors, also have a similar problem as in the humidity sensors.

In conclusion, it is necessary to provide an improved or novel sensor and sensor working method, and the novel sensor should be able to reflect actual environmental parameters of a measured environment quickly and precisely. In a case of a dramatic environmental change, the sensors shall be able to accurately reflect environmental parameters at a current moment as much as possible and make a quick response along with the environmental change.

BRIEF SUMMARY

In order solve one of the above technical problems, the present invention provides an environmental sensor, comprising: a sensing element, configured to sense a real-time sensitive characteristic value for transmission; an integrated circuit, configured to continuously obtain the real-time sensitive characteristic value and a real-time clock signal, and calculate a real-time environmental parameter for storage and output; wherein the integrated circuit is provided with a variational characteristic function corresponding to the sensing element, and under a prediction mode, the integrated circuit uses the variational characteristic function to perform prediction operation according to the real-time environmental parameter and real-time clock signal and at least one group of real-time environmental parameter and real-time clock signal that are previously stored to obtain an actual environmental parameter for storage and sending.

The integrated circuit can also comprise: a storage unit, configured to store the real-time environmental parameter, real-time clock signal and actual environmental parameter; and a predicting unit, provided with the variational characteristic function therein, and configured to perform prediction operation under a prediction mode to obtain the actual environmental parameter.

Under the prediction mode, the integrated circuit is further configured to perform prediction operation according to each or part of subsequent groups of real-time environmental parameters and real-time clock signals to obtain the subsequent actual environmental parameters successively, which are used for correcting the actual environmental parameter previously obtained.

The environmental sensor can also comprise an interruption control unit, configured to receive the actual environmental parameter obtained by the integrated circuit under the prediction mode, and set an upper threshold and/or lower threshold for the next actual environmental parameter according to a predetermined setting parameter. If the actual environmental parameter obtained in the next prediction operation exceeds a range of the upper threshold or lower threshold, the interruption control unit stops the integrated circuit from outputting the actual environmental parameter, and the integrated circuit outputs the next real-time environmental parameter. The sensing element may comprise a humidity-sensitive element and/or a thermosensitive element.

The environmental sensor may also comprise: a signal conditioning module performing signal preprocessing on the real-time sensitive characteristic value and an analog-digital converter; a clock unit, configured to generate a real-time clock signal for recoding sensing time of the sensing element for transmission; a port configured to perform data exchange with an external device.

In another aspect, the present invention further provides a method for measuring and predicting an environmental parameter, which comprises: Step 1, providing a variational characteristic function corresponding to a sensing element; Step 2, continuously obtaining a real-time sensitive characteristic value sensed by the sensing element and a real-time clock signal corresponding to the real-time sensitive characteristic value, and calculating a real-time environmental parameter corresponding to the real-time sensitive characteristic value for storage; Step 3, setting a change range, and comparing the real-time environmental parameter and real-time clock signal with one or more groups of real-time environmental parameters and real-time clock signals that are previously stored; if the change range is not exceeded, outputting the real-time environmental parameter, if the change range is exceeded, performing prediction operation; Step 4, in the prediction operation, using the variational characteristic function to perform prediction operation according to at least two groups of real-time environmental parameters and real-time clock signals to obtain an actual environmental parameter corresponding to an environmental factor for storage and output.

The method, after the step 4, may also comprise: Step 5, in the prediction operation, continuously obtaining a plurality of groups of subsequent real-time sensitive characteristic values and real-time clock signals and calculating a corresponding real-time environmental parameter, and selecting each or part of groups of real-time environmental parameters and real-time clock signals for prediction operation to continuously obtain the subsequent actual environmental parameter; Step 6, correcting the prior actual environmental parameter with the subsequent actual environmental parameter; and Step 7, terminating steps 4-6 when the subsequent actual environmental parameter tends to be stable.

The method, after the step 4 and/or step 5, may also comprise: Step A, setting an upper threshold and/or lower threshold for the next actual environmental parameter according to the currently obtained actual environmental parameter and a predetermined setting parameter; Step B, when the next actual environmental parameter exceeds a range of the upper threshold or lower threshold, terminating the steps 6-7 and outputting the next real-time environmental parameter.

The method, after the step B, may also comprise: Step C, when the subsequently output real-time environmental parameter accords with a change rule and a threshold restriction of the variational characteristic function, or after set time period, restoring to perform the steps 6-7.

In the step 2, the real-time sensitive characteristic value can be subjected to signal conditioning and analog-digital conversion.

The environmental sensor provided by the present invention can make a fast response when entering an environment to be measured, and there is no need to wait for the sensing element to finish sensing completely, an actual environmental parameter highly matched with the environment to be measured can be output. The environmental sensor is suitable for the environment that needs to be quickly measured, and provides a proper platform for actual use of the high-precision sensing element. When using the system, a user can obtain the environmental parameter at first time, and the system can quickly make a correction and response if the environment to be measured is changed. The above design can satisfy quick measurement of the environmental parameter under conditions of daily social life and industrial and agricultural production. In an extreme case that the environmental parameter changes irregularly and dramatically, the prediction operation can be interrupted, a real-time result can be output and a hint is given. Therefore, the environmental sensor provided by the present invention greatly improves a measurement efficiency and precision of the sensor, and makes application of a novel sensitive material with a higher precision but slower response possible. In another aspect, the present invention provides a method for quickly and accurately measuring and predicting the environmental parameter, which is suitable for multiple sensing elements.

DETAILED DESCRIPTION OF VARIOUS EMBODIMENTS

Figure 1:
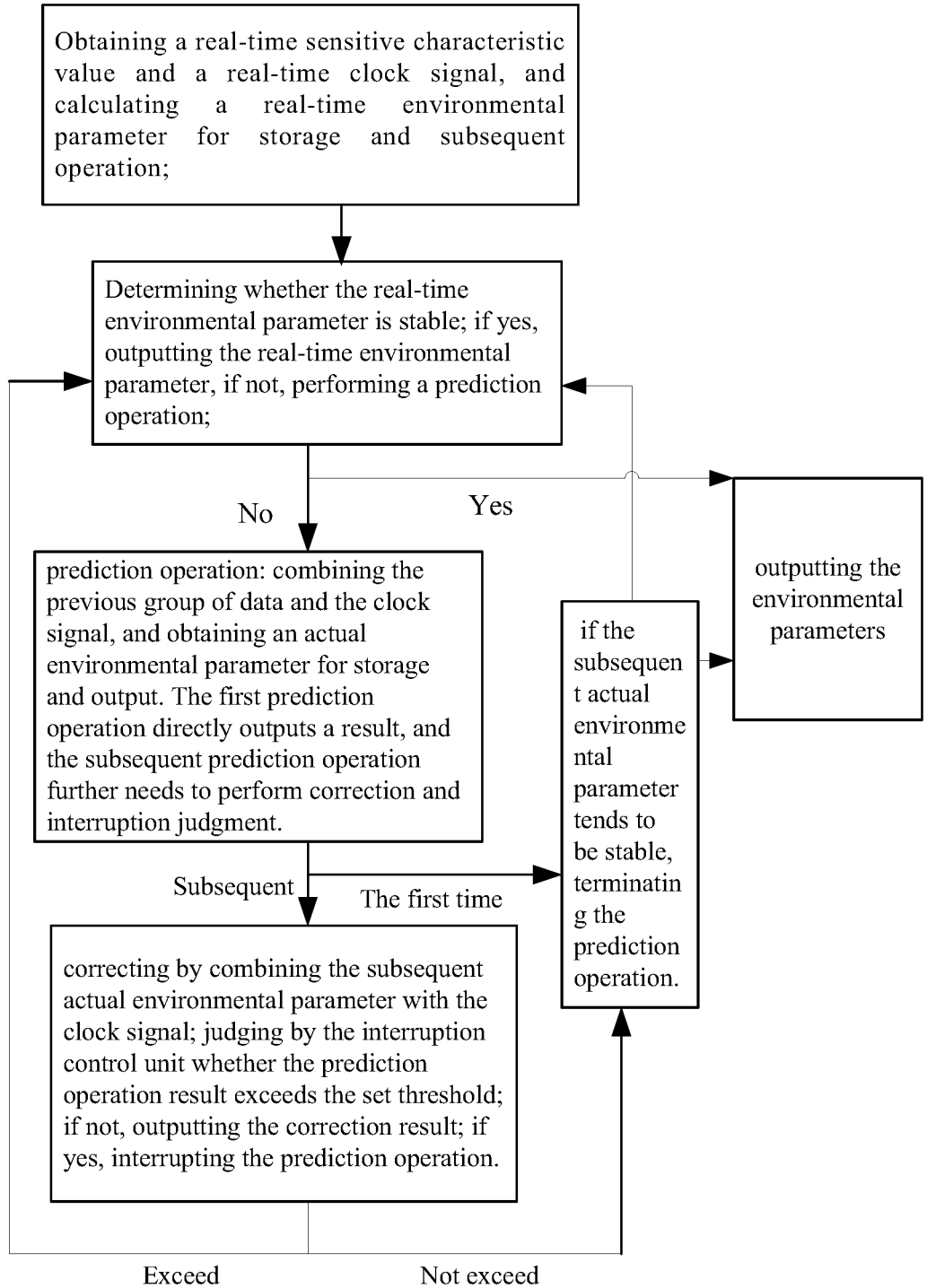
FIG. 1 is a schematic diagram of steps of a method for measuring and predicting an environmental parameter.

Embodiments of the present invention are described in detail as below, examples of the embodiment are shown in drawings, wherein the same or similar reference numerals represent the same or similar components or components having the same or similar functions from beginning to end. The embodiments described with reference to the following drawings are exemplary, and are merely intended for explaining the present invention rather than limiting the present invention. The "environmental factor" indicates a feature in an environment such as temperature, humidity, and concentration of certain chemical substance, etc.; the "environmental parameter" indicates a physical quantity reflecting the "environmental factor", such as degree centigrade, concentration, and mole number, etc.; the "real-time sensitive characteristic value" indicates a sensing condition generated by a sensing element for the "environmental factor" at current moment and an electrical signal is output; the "real-time environmental parameter" indicates an environmental parameter calculated according to the "real-time sensitive characteristic value"; and the "actual environmental parameter" indicates an environmental parameter obtained and output by an integrated circuit which selects a working state according to an actual condition.

Figure 2:
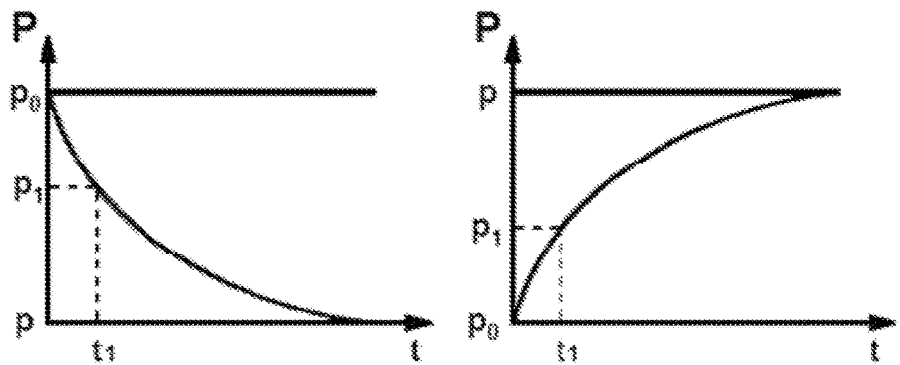
FIG. 2 is a schematic diagram that a sensitive characteristic value of a sensing element is changed along with time in an environment to be measured in a specific embodiment.

The present invention provides a novel method for measuring and predicting an environmental parameter, description on such method and an actual structure are combined together to facilitate understanding. As shown in FIG. 1, the method for measuring and predicting an environmental parameter at least comprises:

Step 1, a variational characteristic function corresponding to a sensing element to be used is provided. When the sensing element is placed in an environment to be measured, the sensing element will make a reaction to a specific environmental factor, and gradually starts to be subjected to physical and/or chemical change to generate a real-time sensitive characteristic value. In general, after the sensing element enters the environment to be measured, its response process has a fixed rule which is mainly dominated by single exponential and multiple exponential functions and their linear combination. As shown in FIG. 2, taking a humidity-sensitive element as an example, with time elapse in the environment to be measured, a humidity sensitive characteristic value will be changed according to a fixed variational function, wherein P represents the sensitive characteristic value, t represents sensing time, $p_0$ represents a sensitive characteristic value of an initial state when the humidity-sensitive element does start to monitor, and p represents an actual sensitive characteristic value of the environment to be measured. Since the sensing element needs a period of time to sense, after entering the environment to be measured for time $t_1$, the real-time sensitive characteristic value of the humidity-sensitive element is $p_1$ rather than p. The variational characteristic function is a function relationship derived from a change relationship between the sensitive characteristic value of the sensing element and the sensing time and can reflect a change relationship between the sensing process and time of the sensing element in the environment to be measured.

Step 2, a real-time sensitive characteristic value sensed by the sensing element and a real-time clock signal corresponding to the real-time sensitive characteristic value is continuously obtained, and a real-time environmental parameter corresponding to the real-time sensitive characteristic value is calculated for storage. The real-time clock signal corresponding to each real-time environmental parameter also needs to be stored. One application specific integrated circuit (ASIC) can be used for collecting the above data, and the real-time clock signal is provided by one clock unit. The integrated circuit can be replaced with other electronic operation units, and a single chip can be used to realize more complex functions when there is no limitation to a device size, which is not limited in the present invention. The real-time clock signal records a time point when the sensing element senses the environment to be measured. For example, a first group of real-time sensitive characteristic values represent variational characteristics that the sensing element enters the environment to be measured, and a first group of real-time clock signals represent a time point when the sensing element enters the environment to be measured. A second group of real-time clock signals reflect the time that the sensing element stays in the environment to be measured, and a second group of real-time sensitive characteristic values reflect the sensitive characteristics generated by the sensing element for the environment to be measured at current moment. The integrated circuit calculates a corresponding real-time environmental parameter with the two real-time sensitive characteristic values, and stores the two real-time environmental parameters and real-time clock signals corresponding to them in a time sequence.

Step 3, a change range is set, the real-time environmental parameter and real-time clock signal are compared with one or more groups of real-time environmental parameters and real-time clock signals that are previously stored, if the change range is not exceeded, the real-time environmental parameter is output, if the change range is exceeded, a prediction operation is performed.

Specifically, those skilled in the art can set a change range according to an actual use condition to measure a change degree of the currently obtained real-time environmental parameter and real-time clock signal relative to the previously stored real-time environmental parameter and real-time clock signal, and decide to perform what processing on the data. The change range is only specific to the real-time environmental parameter, for example, "whether the change degree of the real-time environmental parameter relative to the previously stored real-time environmental parameter is larger than 3%". Or, the change range can be a comprehensive consideration on the real-time environmental parameter and the real-time clock signal, for example, "whether the change degree of the real-time environmental parameter relative to the previously stored real-time environmental parameter is larger than 3%, and a time interval between the real-time clock signal and the real-time clock signal previously stored is smaller than 1s". Using the change range, whether the measured environment has suddenly changed can be judged. If the real-time environmental parameter and real-time clock signal do not exceed the change range, then it is indicated that the measured environment is not obviously changed, and the real-time environmental parameter can be output for ensuring precision. On the contrary, if the change range is exceeded, then it is indicated that the measured environment is changed obviously, and a prediction operation is required.

Step 4, if step 3 judges that the prediction operation is required, the variational characteristic function is used to perform prediction operation according to at least two groups of real-time environmental parameters and real-time clock signals to obtain an actual environmental parameter corresponding to an environmental factor for storage and output.

Specifically, in the prediction operation, the integrated circuit uses the variational characteristic function corresponding to the sensing element to perform prediction operation according to one group of real-time environmental parameters and real-time clock signals and one group of real-time environmental parameters and real-time clock signals previously stored. In other embodiments, the integrated circuit can also perform prediction operation according to two groups of real-time environmental parameters and real-time clock signals previously stored. Take the case that the real-time environmental parameter serves as a prediction basis as an example. First, a difference $\Delta E$ between the real-time environmental parameter and the real-time environmental parameter previously stored is calculated, a difference $\Delta t$ between a second group of real-time time signal t1 and a first group of real-time time signal t0 is calculated. According to $\Delta E$ and $\Delta t$ and the variational characteristic function, an actual environmental parameter basically matched with the actual environmental factor can be predicted. That is, the environmental parameter corresponding to the real-time sensitive characteristic value generated after the sensing element fully senses for a period of time.

According to the above method, the sensor can make a response to the environment to be measured fast and accurately. The method also comprises the following steps after the step 4:

Step 5, in the prediction operation, a plurality of groups of subsequent real-time sensitive characteristic values and real-time clock signals are continuously obtained and a corresponding real-time environmental parameter is calculated for storage, each or part of groups of real-time environmental parameters and real-time clock signals are selected for prediction operation to continuously obtain the subsequent actual environmental parameters;

Step 6, the prior actual environmental parameter is corrected with the subsequent actual environmental parameter; and Step 7, steps 4-6 are terminated when the subsequent actual environmental parameter tends to be stable.

Specifically, the sensing element continuously generates the real-time sensitive characteristic values, the integrated circuit successively obtains the newly-generated groups of real-time sensitive characteristic values and real-time clock signals, and calculates the real-time environmental parameter for the subsequent real-time sensitive characteristic values for storage. The integrated circuit obtains a difference between the subsequently obtained various groups of data and various previously-stored groups of data, repeatedly performs the prediction operation and calculates the subsequent actual environmental parameters. Since the subsequently generated real-time sensitive characteristic values are closer to an actual condition of the environment to be measured, the predicted actual environmental parameter is more accurate, and the integrated circuit may correct the prior actual environmental parameter with the newly-calculated actual environmental parameter. The correction may be a direct replacement of the prior actual environmental parameter, and may also be amendment to the prior actual environmental parameter through specific operation processing. When the plurality of subsequently obtained actual environmental parameters tends to be stable, the prediction operation is terminated, i.e., steps 4-6 are terminated. At this point, the current actual environmental parameter obtained by prediction operation and the real-time environmental parameter are basically consistent, and both the subsequent real-time environmental parameter and the actual environmental parameter are not changed greatly. Therefore, the prediction operation may be terminated, and the real-time environmental parameter is directly output.

Particularly, the method for measuring and predicting an environmental parameter according to the present invention can comprise a method for measuring a frequent and irregular change due to environmental factors. The method, after the step 4 and/or step 5, may also comprise:

Step A, setting an upper threshold and/or lower threshold for the next actual environmental parameter according to the currently-obtained actual environmental parameter and a predetermined setting parameter;

Step B, when the next actual environmental parameter exceeds a range of the upper threshold or lower threshold, the steps 6-7 are terminated and the next real-time environmental parameter is output; and Step C, when the subsequently-output real-time environmental parameter conforms to a change rule and a threshold restriction range of the variational characteristic function, or after pre-set time period, the steps 6-7 are restored.

Specifically, according to factors such as an actual precision requirement, a sensitivity requirement, and a measured environment, those skilled in the art can give a setting parameter in the integrated circuit in advance. An upper threshold and/or lower threshold can be set after the setting parameter adds a redundancy to the actual environmental parameter obtained every time. When the method for measuring and predicting the environmental parameter is carried out in steps 4 and 5, the integrated circuit compares the subsequent actual environmental parameter with the prior actual environmental parameter, if the subsequent actual environmental parameter exceeds a range of the upper threshold or lower threshold, that is, the subsequent actual environmental parameter is not regularly changed according to the variational characteristic function, it is indicated that the environmental factors to be measured are irregularly changed. At this point, the integrated circuit can interrupt the execution of steps 6 and 7, that is, actual environmental parameters are not output any more. The integrated circuit can directly output the subsequent real-time environmental parameter. After the execution of the steps 6 and 7 is interrupted, the integrated circuit can continuously monitors the real-time environmental parameter, and when a change condition of the subsequent real-time environmental parameter conforms to the change rule of the variational characteristic function again, the integrated circuit can restore execution of the steps 6 and 7. Those skilled in the art may also set a duration for interruption of the steps 6 and 7. After being interrupted for certain period of time, the steps 6 and 7 are restored automatically. In addition, the integrated circuit can still monitor the actual environmental parameter obtained in step 5 after interrupting the steps 6 and 7, and can restore the steps 6 and 7 after the subsequently obtained actual environmental parameter is returned to the range of the upper threshold and lower threshold.

Particularly, those skilled in the art can adjust the above setting parameter according to actual application conditions, by increasing or decreasing a distance between the upper threshold and the lower threshold, the sensor can adapt to different environmental characteristics, and an objective of precisely reflecting the environmental factors and/or making a quick reaction to the change of the environmental factors can be achieved.

The foregoing is the method for measuring and predicting the environmental parameter of the present invention, and the method may output an actual environmental parameter basically matched with an actual condition of the environmental factors without a need to wait for sufficient sensing by the sensing element, the waiting time used by a sensitive system is greatly reduced, and application of a humidity-sensitive element with higher precision and other sensing elements is made possible.

The method may also comprises other steps of signal processing, for example, in the step 2, the real-time sensitive characteristic value can be subjected to signal conditioning and analog-digital conversion firstly. The signal conditioning comprises a signal conditioning process such as filtering and rectifying, and signals of the real-time sensitive characteristic value are conditioned to a proper form. The real-time sensitive characteristic value is an analog signal which may be converted to a digital signal for facilitating a subsequent estimation operation.

The method for measuring and predicting the environmental parameter of the present invention is suitable for multiple sensing elements, what is used in the above embodiment is a humidity-sensitive element, and the present invention does not limit a type of the sensing element, for example, the sensing element may comprise a humidity-sensitive element and a thermosensitive element, which are combined for measuring a relative humidity of the environment. Those skilled in the art may combine the method for measuring and predicting an environmental parameter with other sensing elements according to use purposes.

Figure 3:
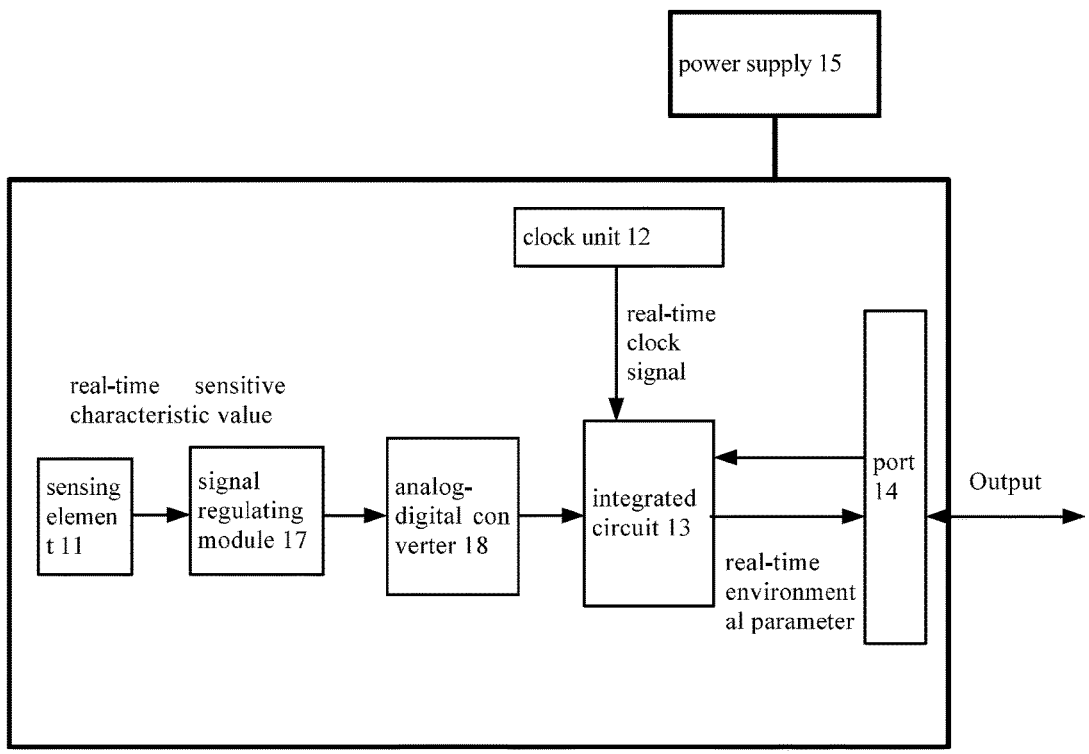
FIG. 3 is a schematic diagram of a system of an environmental sensor provided in a specific embodiment of the present invention.

In another aspect, the present invention further provides an environmental sensor implementing the above method for measuring and predicting an environmental parameter, and as shown in FIG. 3, the environmental sensor at least comprises: a sensing element 11 and an integrated circuit 13.

The sensing element 11 is configured to sense an environment factor of the environment to be sensed to generate a real-time sensitive characteristic value for transmission. The environmental sensor needs to record sensing time information of the sensing element 11, therefore, the environmental sensor may comprise a clock unit 12 configured to record the sensing time of the sensing element 11, and the clock unit 12 provides a real-time clock signal. Or the sensor may obtain a real-time clock signal from an external device, and the real-time clock signal can be transmitted to the integrated circuit 13 from the outside. The integrated circuit 13 can continuously obtain a real-time sensitive characteristic value and the real-time clock signal, and operates to obtain a real-time environmental parameter for storage and output. In a specific embodiment, a variational characteristic function corresponding to the sensing element 11 is preset in the integrate circuit 13. Under a common mode, the integrated circuit 13 can directly output the obtained real-time environmental parameter, and when prediction operation is required, the integrated circuit 13 may enter a prediction mode, and uses the variational characteristic function to perform prediction operation according to the real-time environmental parameter and real-time clock signal and at least one group of real-time environmental parameter and real-time clock signal that are previously stored to obtain an actual environmental parameter corresponding to the environmental factors.

Figure 4:
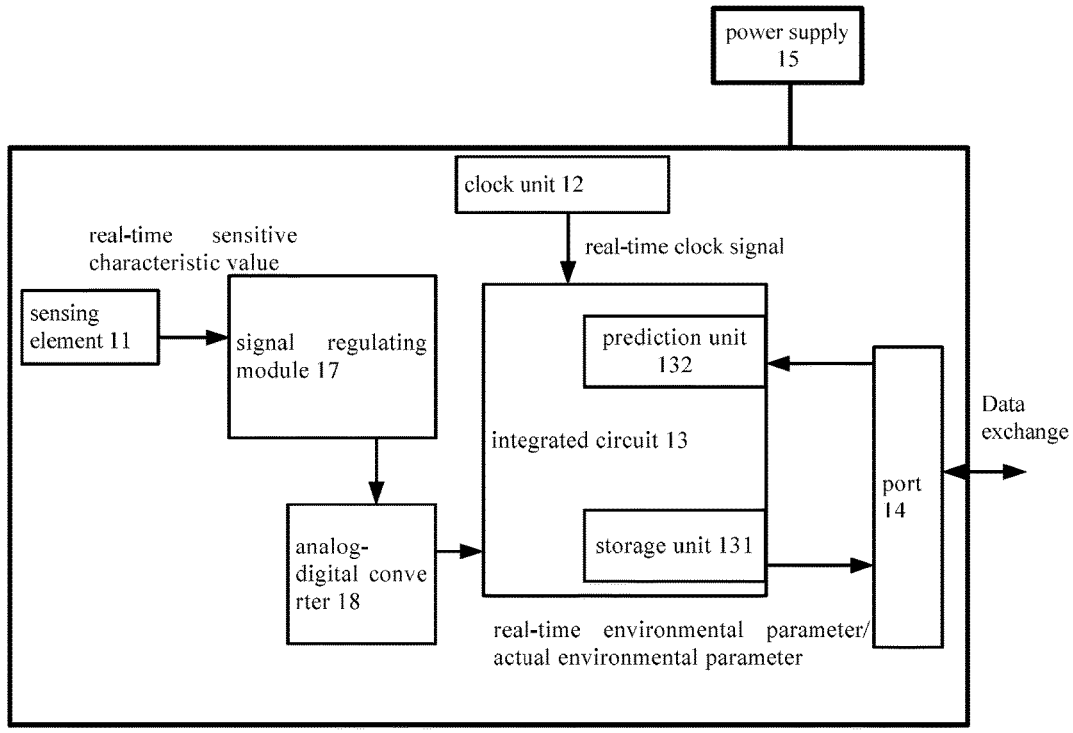
FIG. 4 is a schematic diagram of a system of an environmental sensor provided in a specific embodiment of the present invention.

Preferably, as shown in FIG. 4, the integrated circuit 13 may comprise a storage unit 131 configured to store the real-time environmental parameter, real-time clock signal and actual environmental parameter. Data received and operated by the integrated circuit 13 can be stored in the storage unit 131. The integrated circuit 13 further comprises a predicting unit 132 configured with the variational characteristic function therein, and under a prediction mode, the predicting unit 132 is configured to perform prediction operation to obtain the actual environmental parameter. The integrated circuit 13 may send and store the actual environmental parameter. Those skilled in the art can set the integrated circuit 13 in advance, and limits a change range of the real-time environmental parameter obtained every time, if the real-time environmental parameter obtained next time exceeds the change range, then the integrated circuit 13 is switched to the prediction mode from a common mode.

Further, under the prediction mode, the integrated circuit 13 is further configured to perform prediction operation according to each or part of subsequent groups of real-time environmental parameters and real-time clock signals to obtain the subsequent actual environmental parameters successively. Preferably, the subsequent actual environmental parameter corrects the environmental parameter obtained previously.

Figure 5:
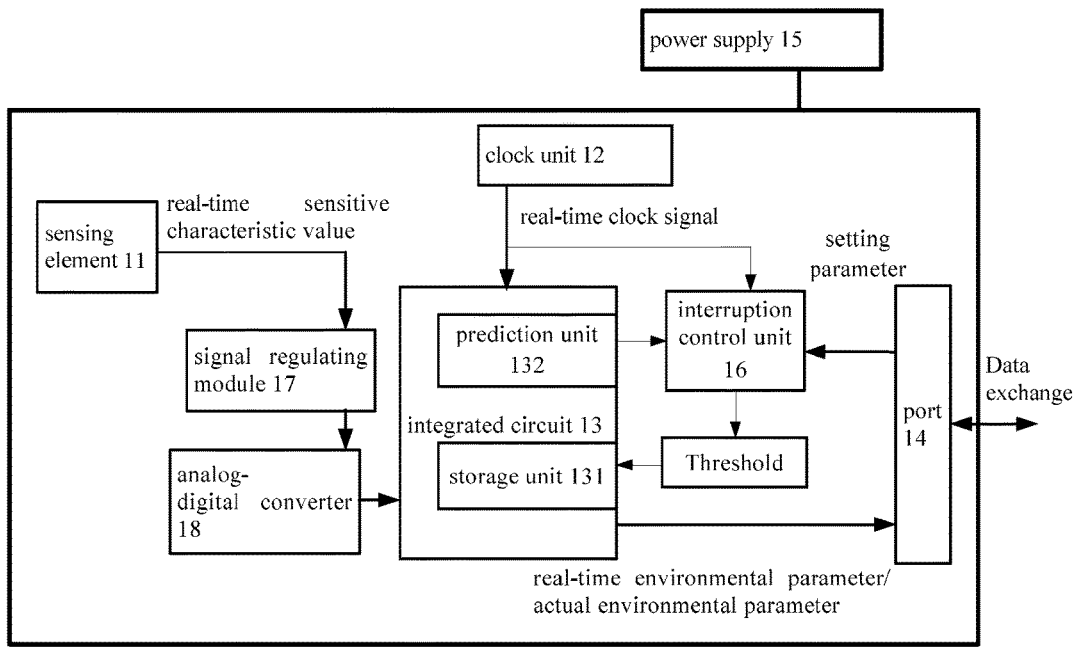
FIG. 5 is a schematic diagram of a system of an environmental sensor provided in a specific embodiment of the present invention.

Particularly, in order to deal with the a condition that the environment to be measured is frequently and irregularly changed, as shown in FIG. 5, the environmental sensor of the present invention may further comprise an interruption control unit 16 configured to receive the actual environmental parameter and the real-time clock signal obtained by the integrated circuit 13 under the prediction mode, and set an upper threshold and/or lower threshold for the next actual environmental parameter according to a predetermined setting parameter. If the actual environmental parameter obtained in the next prediction operation exceeds a range of the upper threshold or lower threshold, the interruption control unit 16 stops the integrated circuit 13 from outputting the actual environmental parameter, and the integrated circuit 13 outputs the next real-time environmental parameter. Those skilled in the art can freely select the setting parameter according to an actual use condition of the environmental sensor and requirements on precision and sensitivity.

In addition, the sensing element 11 may be a sensitive device such as a humidity-sensitive element and/or a thermosensitive element and combination thereof, and configured to monitor the environmental factors such as relative humidity and temperature.

The environmental sensor may further comprise a signal conditioning module 17 and a analog-digital converter 18. The signal conditioning module 17 performs signal processing such as filtering and rectifying on the real-time sensitive characteristic value generated by the sensing element 11. The real-time sensitive characteristic value is an analog signal, and is converted to a digital signal by the analog-digital converter 18 to facilitate subsequent estimation operation on the signal.

The environmental sensor may also comprises a port 14 configured to perform data exchange with an external device. Output of the actual environmental parameter, input of the time signal can be both finished by the port 14. The sensor can use I$^2$C port 14 or other port protocols. The external device may be a computer, a monitoring device or a mobile electronic device, and the present invention does not limit a type of the port 14 and the external device. In addition, the environmental sensor may further comprise an independent power supply source 15, and may also obtain electric energy from the external device.

The foregoing is the environmental sensor provided by the present invention, and the system realizes accurate prediction on the environmental factors of the environment to be predicted through a variational characteristic function corresponding to the sensing element. The environmental sensor may output an actual environmental parameter basically matched with the environmental factors without a need to wait for complete sensing of the sensing element. As the sensing element finishes sensing continuously, the system corrects the actual environmental parameter previously generated to enable it to be further approximate to the environmental factors. And this makes actual application of the sensing element having higher precision but requiring longer sensing time possible. In addition, when irregular change of the environmental factors occurs frequently, the system may not output the result of a prediction operation and directly output the real-time environmental parameter which is matched with the environmental factors as much as possible.

An application range of the present invention is not limited to the embodiments specific to the humidity-sensitive and thermosensitive elements described above, and those skilled in the art may adjust the features of the type of the sensing element, the variational characteristic function, and the range of the threshold, etc. A time unit may be disposed in the environmental sensor, and a real-time clock signal may be received from an external device. The invention has a principle that the variational characteristic function of the sensing element is used to predict the actual environmental parameter, and a true environmental parameter is obtained before the sensing element finishes the sensing, and fast response of the sensor may be realized. In another aspect, in a case that fast and irregular change occurs to the environment to be measured, the sensing system may cancel output of a prediction operation result, and directly output the real-time environmental parameter to reflect the current environmental factors as true as possible.

Those skilled in the art may make various changes, modifications, replacements and transformations to these embodiments without departing from the principle and spirit of the present invention, and claims appended to the present invention aim to contain these transformations and replacements in its protection scope.

What is claimed is:
1. An environmental sensor, comprising:
a sensitive device (11), configured to sense a real-time sensitive characteristic value for transmission;
an interruption control unit (16); and
an application specific integrated circuit (ASIC) (13), configured to continuously obtain the real-time sensitive characteristic value and a real-time clock signal, and calculate a real-time environmental parameter for storage and output,
wherein:
the ASIC (13) uses a variational characteristic function corresponding to the sensitive device (11) when the ASIC (13) is working under a prediction mode to perform prediction operation according to the real-time environmental parameter and real-time clock signal and at least one group of real-time environ- mental parameter and real-time clock signal that are previously stored to obtain an actual environmental parameter for storage and transmission;

under the prediction mode, the ASIC (13) is further configured to perform prediction operation according to each or part of subsequent groups of real-time environmental parameters and real-time clock signals to obtain the subsequent actual environmental parameters successively so as to correct the actual environmental parameter previously obtained;

the interruption control unit (16) comprises a processor configured to: receive the actual environmental parameter obtained by the ASIC (13) under the prediction mode, and set an upper threshold and/or lower threshold for the next actual environmental parameter according to a predetermined setting parameter; and if the actual environmental parameter obtained in the next prediction operation exceeds the upper threshold or lower threshold, the processor stops the ASIC (13) from outputting the actual environmental parameter, and the ASIC (13) outputs the next real-time environmental parameter.

2. The environmental sensor according to claim 1, wherein the ASIC (13) comprises a storage module (131) configured to store the real-time environmental parameter, real-time clock signal, and actual environmental parameter.

3. The environmental sensor according to claim 1, wherein the ASIC (13) comprises a predicting module (132), provided with the variational characteristic function therein and configured to perform prediction operation and obtain the actual environmental parameter.

4. The environmental sensor according to claim 1, further comprising a clock unit (12), which comprises a processor configured to generate a real-time clock signal for recording sensing time of the sensitive device (11) for transmission.

5. A method for measuring and predicting an environmental parameter, the method comprising the steps of:

setting, in an application specific integrated circuit (ASIC) (13), providing a variational characteristic function corresponding to a sensitive device (11);

continuously obtaining, via the ASIC (13), a real-time sensitive characteristic value sensed by the sensitive device (11) and a real-time clock signal corresponding to the real-time sensitive characteristic value, and calculating a real-time environmental parameter corresponding to the real-time sensitive characteristic value for storage;

setting, via the ASIC (13), a change range, and comparing, via the ASIC (13), the real-time environmental parameter and real-time clock signal with one or more groups of real-time environmental parameters and real-time clock signals that are previously stored; if the change range is not exceeded, outputting, via the ASIC (13), the real-time environmental parameter, and if the change range is exceeded, performing, via the ASIC (13), a prediction operation; and in the prediction operation, using the variational characteristic function to perform, via the ASIC (13), the prediction operation according to at least two groups of real-time environmental parameters and real-time clock signals to obtain an actual environmental parameter corresponding to an environmental factor for storage and output;

in the prediction operation, continuously obtaining, via the ASIC (13), a plurality of groups of subsequent real-time sensitive characteristic values and real-time clock signals and calculating a corresponding real-time environmental parameter, and selecting each or part of groups of real-time environmental parameters and real-time clock signals for prediction operation to continuously obtain the subsequent actual environmental parameter;

correcting, via the ASIC (13), the prior actual environmental parameter with the subsequent actual environmental parameter;

terminating, via the ASIC (13), the using, continuously obtaining, and correcting steps when the subsequent actual environmental parameter tends to be stable; and after at least one of the using or the continuously obtaining steps is completed:

setting, by a processor, an upper threshold and/or lower threshold for the next actual environmental parameter according to the currently obtained actual environmental parameter and a predetermined setting parameter; and when the next actual environmental parameter exceeds the upper threshold or lower threshold, terminating, by the processor, the correcting and the terminating steps and outputting the next real-time environmental parameter.

6. The method according to claim 5, further comprising, after the outputting step and either when the subsequently output real-time environmental parameter accords with a change rule and a threshold restriction of the variational characteristic function or after a set time period, restoring, via the processor, performance of the correcting and terminating steps.

* * * * *